United States Patent
Tindel

[11] Patent Number: 5,807,237
[45] Date of Patent: Sep. 15, 1998

[54] ENDOSCOPIC DEVICE

[76] Inventor: Nathaniel L. Tindel, 19 Lighthouse Rd., Great Neck, N.Y. 11024

[21] Appl. No.: 829,179

[22] Filed: Mar. 31, 1997

[51] Int. Cl.[6] .......................................................... A61B 1/04
[52] U.S. Cl. ............................................................... 600/114
[58] Field of Search ...................................... 600/102, 105, 600/114, 138, 139, 135, 146; 604/264, 164

[56]  References Cited

U.S. PATENT DOCUMENTS

| | | |
|---|---|---|
| 3,256,875 | 6/1966 | Tsepelev et al. . |
| 3,818,902 | 6/1974 | Kinoshita et al. . |
| 3,896,793 | 7/1975 | Mitsui et al. . |
| 3,918,438 | 11/1975 | Hayamizu et al. . |
| 4,697,577 | 10/1987 | Forkner . |
| 4,805,597 | 2/1989 | Iwakoshi . |
| 4,832,473 | 5/1989 | Ueda . |
| 4,838,247 | 6/1989 | Forkner . |
| 4,846,154 | 7/1989 | MacAnally et al. . |
| 4,852,550 | 8/1989 | Koller et al. . |
| 5,179,934 | 1/1993 | Nagayoshi et al. . |
| 5,554,100 | 9/1996 | Leiner et al. . |

*Primary Examiner*—Beverly M. Flanagan
*Attorney, Agent, or Firm*—Collard & Roe, P.C.

[57]  ABSTRACT

The invention is an endoscopic and cannula system for viewing internal parts of a human body, comprising an endoscope and a cannula. The endoscope comprises an elongated extension tube, which has, at its proximal end, a control body and, at its distal end, a flexible fiber optic tip. An ocular eyepiece is attached to the control body and is adapted to permit visualization through the endoscope to the area to be viewed. A manually controlled flexible fiber optic tip is attached to the distal end of the extension tube and has a lens attached to its distal end. The control body has knobs for adjusting the position and/or direction of the flexible fiber optic tip. The cannula comprises a hollow tube for receiving the endoscope and has means for moving the endoscope between a cannula-extended position and a cannula-retracted position. In the cannula-extended position, the flexible fiber optic tip is located entirely within the cannula, and in the cannula-retracted position, the manually controlled flexible fiber optic tip extends beyond the distal end of the cannula.

9 Claims, 5 Drawing Sheets

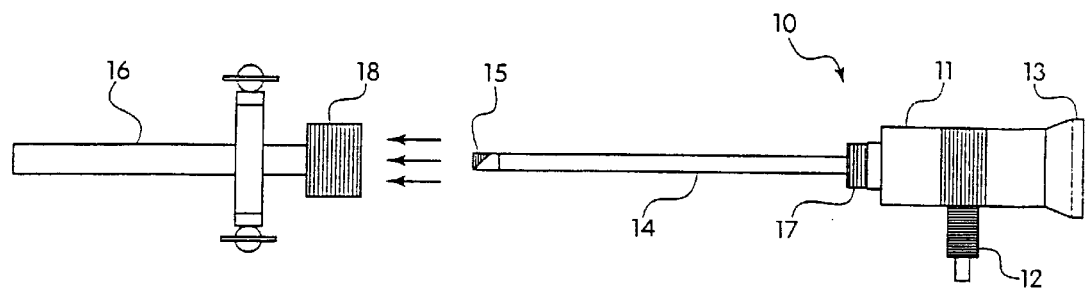
Fig. 1a - Prior Art
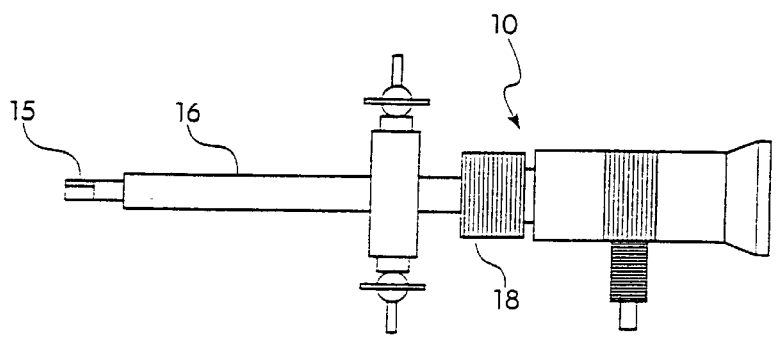
Fig. 1b - Prior Art
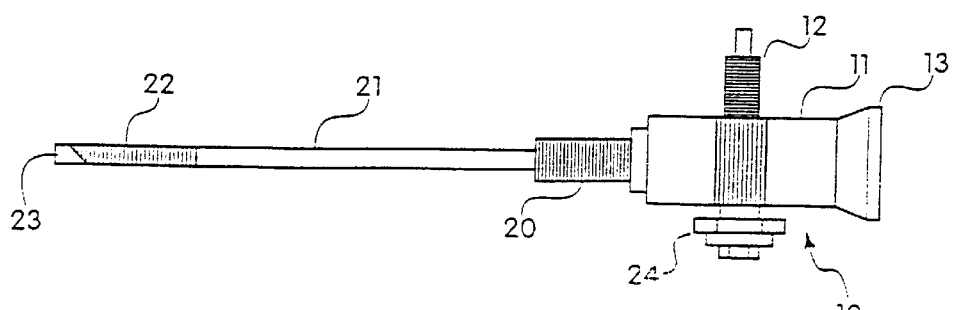
Fig. 2

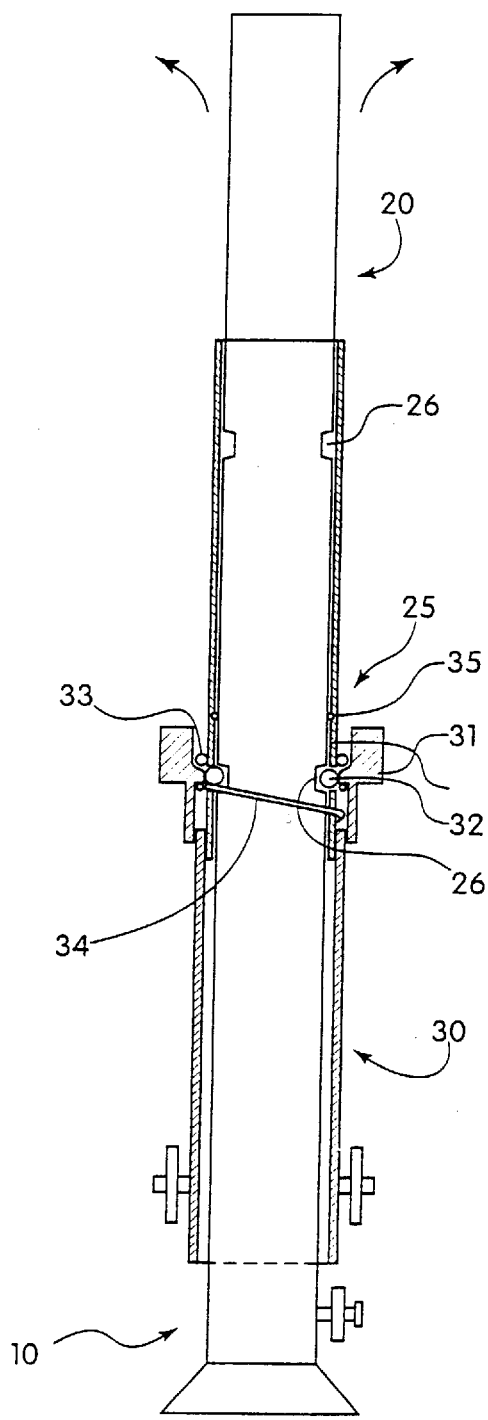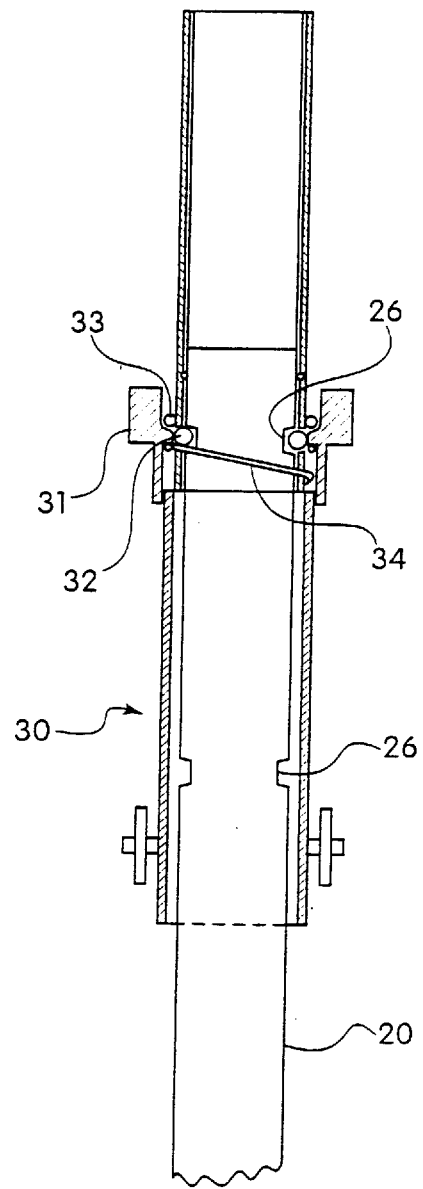
Fig. 5
Fig. 6

ENDOSCOPIC DEVICE

BACKGROUND OF THE INVENTION

1. Field of the Invention

This invention relates to a device for performing endoscopic surgery (including, but not limited to, arthroscopy, laparoscopy, thoracoscopy, spinoscopy and endoscopy). In particular, the invention relates to a rigid endoscope having a manually controlled flexible fiber optic tip that can be maneuvered during surgery to increase the viewing field, and a cannula for positioning the endoscope in two different ways.

2. The Prior Art

Surgical endoscopic procedures use different instruments depending on the flexibility of the instrument required. Some endoscopes are rigid, some are flexible by means of a fiber optic mechanism, and some combine a rigid endoscope with a manually controlled flexible fiber optic tip. Furthermore, certain endoscopic procedures require the use of a hollow cannula to house the endoscope during the procedure. These instruments are labeled in reference to the body cavity, potential space or joint to which they are inserted as follows: laparoscope (abdomen/pelvis), thoracoscope (thorax), spinoscope (spine), and arthroscope (joint). When used with a cannula, prior art instruments have been of the rigid construction type. This discussion pertains to endoscopes used in conjunction with a cannula.

These prior art endoscopes are similar in that they are generally composed of no less than five parts: a rigid extension tube that transmits light fibers to and from the lens and eyepiece; an ocular eyepiece through which light is transmitted from the area viewed; a mechanism for transmitting light from an external light source through the scope to the area being viewed; a locking mechanism to lock the endoscope and cannula together; and a lens located at the distal tip of the rigid extension tube. An example of such an endoscope is described in U.S. Pat. No. 4,838,247.

Rigid endoscopes differ from one another in many physical respects. Among major differences are: (1) the dimensions of the extension tube (in particular, the outside diameter and length, based on the size of the potential space, joint or cavity to be viewed); and (2) the angle of the mounted lens at the end of the rigid extension tube on the endoscope. The lens for each endoscope is mounted at a fixed angle measured between a line drawn perpendicular to the face of the lens and one drawn along the longitudinal axis of the extension tube.

The surgical procedure of rigid endoscopy requires the use of a cannula which is a hollow rigid sheath. The cannula provides a "tunnel" between the cavity, joint or potential space being viewed and the "outside world". Through the cannula, different endoscopes are inserted and withdrawn, one at a time, to view the cavity, joint or potential space. The cannula has several functions which include, but are not limited to, allowing the rapid exchange of endoscopes during the procedure, protecting the lens (which is fragile) at the end of the endoscope, keeping soft tissue away from the endoscope, and maintaining the fluid or air content of the cavity, joint or potential space.

In practice, the cannula stays in place for the duration of the surgical procedure, acting as conduit between the outside world and the cavity, joint or potential space being viewed. An endoscope inserted into the cannula has a uniquely angled lens mounted at its distal tip. Thus, each endoscope inserted into the cannula offers a different viewing angle through which the cavity, joint or potential space is viewed, depending on the angle of the mounted lens. There is a locking mechanism on the cannula which fits into a reciprocal locking mechanism on the endoscope. This locks the endoscope to the cannula once the endoscope is fully inserted into the cannula. An example of such a locking mechanism is described in U.S. Pat. No. 4,852,550. With the endoscope fully inserted and locked into the cannula, the cannula and endoscope act as a single unit that is maneuvered around the cavity, joint or potential space. The endoscope is manually unlocked and withdrawn from the cannula at any point during the procedure. In the fully inserted, locked position, a small portion of the tip of the endoscope, which houses the mounted lens, protrudes beyond the tip of the cannula. This protrusion allows for side viewing with the angled viewing lenses.

The advantage of the rigid endoscope and cannula system is the excellent viewing capability of objects in the viewing field of the lens. The straight cannula and scope provides rigidity in situations where inflexibility of the system is required for adequate viewing. There are disadvantages to the rigid endoscope and cannula system. In particular, the rigid endoscope and cannula system cannot view beyond an obstacle without moving, withdrawing, redirecting and/or rotating the endoscope and cannula system. This requires enough room to maneuver and is not always successful in fixed spaces, such as a joint. Furthermore, in maneuvering the endoscope and cannula system within restricted confines, damage can be done to the cavity, joint or potential space. For example, when used within a joint, the surface tissue lining the joint, called cartilage, can be scraped, scratched, etched, compressed, crushed or otherwise inadvertently damaged by the rigid parts of the system. If at all possible, it is best to avoid damaging any tissue lining the cavity, joint or potential space being viewed.

SUMMARY OF THE INVENTION

It is therefore an object of the present invention to overcome the drawbacks of the prior art and to provide an endoscopic system that is capable of enhanced viewing capacity.

It is another object of the present invention to provide an endoscope and cannula system with a flexible or deflectable tip that can be manually controlled to access difficult and hard to reach cavities, joints or potential spaces within the human body.

It is yet another object of the invention to provide an endoscope and cannula system that provides for manual control of a flexible fiber optic tip that can be converted to a traditional rigid endoscope and cannula system when desired.

The invention comprises an endoscopic system consisting of two parts: an endoscope and a cannula. The endoscope is comprised of a control body attached to the proximal end of an elongated tube; a light source and a light source cable attached to the control body for supplying light to the endoscope; an ocular eyepiece attached to the control body; and a flexible fiber optic tip attached to the distal end of the rigid extension tube. A lens is attached to the end of the flexible fiber optic tip. The cannula is comprised of a rigid hollow tube with a locking mechanism at the proximal end to lock the endoscope. A short distance from the proximal end are valves that permit water or air to enter or exit the cavity, joint or potential space being viewed.

The cannula comprises a hollow rigid tube that can be inserted through skin and soft tissue into the cavity, joint or potential space being viewed. A multiple position docking mechanism is provided on the cannula, which allows the endoscope to reside in one of several working positions while housed within in the cannula, including cannula-retracted and cannula-extended positions.

During use, the endoscope is inserted into a cannula that has been inserted into a cavity, joint or potential space within the human body. Light from the light source travels down the elongated extension tube and illuminates the cavity, joint or potential space to be observed. A video feed placed on the eyepiece can create an image transmitted to a monitor for viewing by the surgeon.

In the cannula-extended position, the endoscope is inserted into the cannula with the flexible fiber optic tip housed entirely within the cannula. In this position, the endoscope operates as a traditional, rigid endoscope.

In the cannula-retracted position, the endoscope resides within the cannula with the flexible fiber optic tip protruding beyond the tip of the cannula. In this position, movement of the flexible tip is possible. The flexible fiber optic tip can be directed into different positions with the deflection knobs located on the control body. The flexible tip can be steered in any direction required, for example, up/down, right/left, etc. Once a desired position is obtained, the tip can be locked in place using the deflection tip locking mechanism. This locking mechanism keeps the tip from moving while viewing and permits hands-free operation of the deflection mechanism.

In one embodiment of the endoscope and cannula system, the endoscope is locked and unlocked in several positions with respect to a single-piece tube cannula. For example, when initial viewing is required with the rigid system characteristics, the endoscope is inserted into the cannula and locked into the cannula-extended position.

Should an obstructed area require viewing, the endoscope can be unlocked from the cannula-extended position and the endoscope is advanced further into the cannula into the cannula-retracted position. In this position, the flexible fiber optic tip extends beyond the cannula and is available for flexible operation with the deflection knobs. If a rigid endoscope is required again, the flexible tip can be straightened using the deflection knobs and the endoscope can be unlocked from the cannula, withdrawn to the first, cannula-extended position, and the endoscope is locked back into the cannula in the first position.

In an alternative embodiment, it is the cannula it self that moves to position itself with respect to the endoscope. The cannula can be built so that it is made from two tubular sections, with one section telescopically sliding within the other. The inner section may be slid within the outer section to allow the fiber optic tip to protrude from the cannula at desired times. The cannula contains two locking devices. One is to lock the endoscope to one section of the cannula near the control head. An example of such a locking device is described in U.S. Pat. No. 4,852,550. The second is to lock the two sliding sections of the cannula into one of at least two desired positions.

Therefore, the present invention provides the opportunity of using the endoscope and cannula system both as a traditional, rigid endoscope, which has many advantages and is appropriate for many types of procedures, and also as a flexible endoscope, having greatly increased viewing capabilities and offering superior accessibility of hard-to-reach areas of cavities, joints or potential spaces.

BRIEF DESCRIPTION OF THE DRAWINGS

Other objects and features of the present invention will become apparent from the following detailed description considered in connection with the accompanying drawings. It is to be understood, however, that the drawings are designed as an illustration only and not as a definition of the limits of the invention.

In the drawings, wherein similar reference characters denote similar elements throughout the several views:

FIG. 1a is a side view of a prior art endoscope prior to being inserted into a cannula;

FIG. 1b is a side view of a prior art endoscope inserted into a cannula;

FIG. 2 is a side view of the endoscope according to the present invention;

FIG. 5 is a longitudinal sectional view of the cannula and endoscope according to the present invention locked in the cannula-retracted position;

FIG. 6 is a longitudinal sectional view of the cannula and endoscope according to the present invention locked in the cannula-extended position;

DETAILED DESCRIPTION OF THE PREFERRED EMBODIMENTS

Figure 3A:
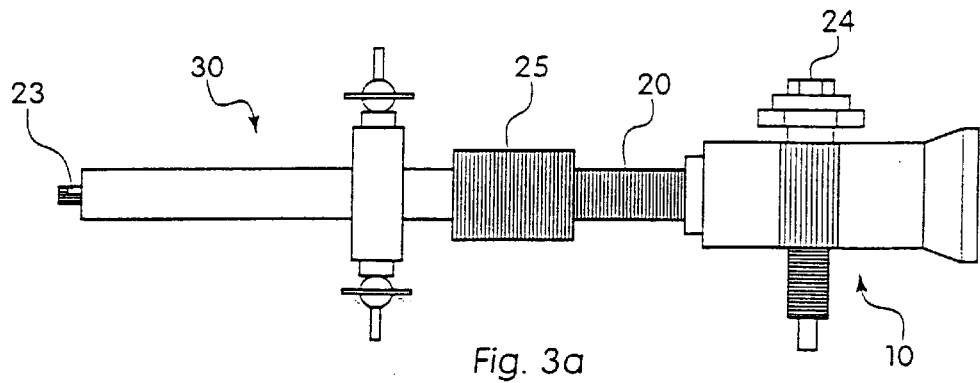
FIG. 3a is a side view of the endoscope and cannula according to the present invention in the cannula-extended position.

Turning now in detail to the drawings, and in particular, FIGS. 1a and 1b, there is shown a typical rigid endoscope and cannula according to the prior art. Endoscope 10 is comprised of control head 11, ocular eyepiece 13, light source 12, tube 14 and lens 15. Endoscope 10 is made to be inserted within cannula 16, as shown in FIG. 1a. A locking mechanism comprised of element 17 on endoscope 10 and element 18 on cannula 16, engages to lock the endoscope in place while it is being used. In use, light from light source 12 travels from control head 11, through extension tube 14 and illuminates the operation area. A viewer or video feed looking into eyepiece 13 looks through lens 15 at the illuminated area.

The prior art endoscope can be locked into the cannula in only one position, with the lens of the endoscope protruding slightly outward from the cannula.

FIG. 2 shows the endoscope according to the present invention. Like the prior art endoscope, the present invention has a control body 11 connected to a light source 12. Tube 21 extends from control body 11 and is connected at its distal end to flexible fiber optic tip 22. Tip 22 is capable of bending in several different directions to enable the viewer to see an expanded section of the operation area. Lens 23 is arranged on the end of flexible fiber optic tip 22.

Control knobs 24 are located on control body 11. Control knobs 24 are connected with flexible fiber optic tip 22 so that turning one or more control knobs 24 moves flexible fiber optic tip 22 into a desired position. This operation is well known in the art and is not described in detail here. An example of the working connection between a flexible tip and a control section is described in U.S. Pat. No. 3,256,875, the disclosure of which is incorporated herein by reference.

Figure 3B:
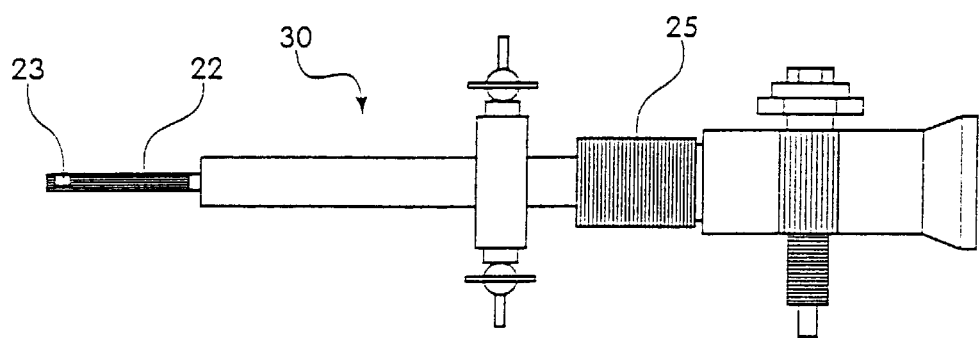
FIG. 3b is a partial side view of the endoscope and cannula according to the present invention in the cannula-retracted position.

FIGS. 3a and 3b show the endoscope of the present invention as it is inserted into a cannula 30 in two different positions. Element 20 on endoscope 10 engages element 25 on cannula 30 to lock endoscope 10 into cannula 30 in a secure way. In the present invention, elements 20 and 25 are configured so as to enable the locking of endoscope 10 in two different positions, a cannula-extended position, as shown in FIG. 3a, and a cannula-retracted position, as shown in FIG. 3b. The dual positioning locking mechanism of endoscope 10 within cannula 30 can be accomplished in many different ways, such as with releasable locks, screws, or any other appropriate means.

In the cannula-extended position shown in FIG. 3a, the device according to the present invention operates in the same manner as the traditional endoscope shown in FIG. 1, i.e. the lens is in a fixed position and the endoscope is rigidly positioned within the cannula. However, during use, the viewer may desire to switch the viewing angle, or position the lens so as to be able to see otherwise inaccessible areas of the body. In this case, the endoscope can be moved into the cannula retracted-position shown in FIG. 3b.

Figure 4:
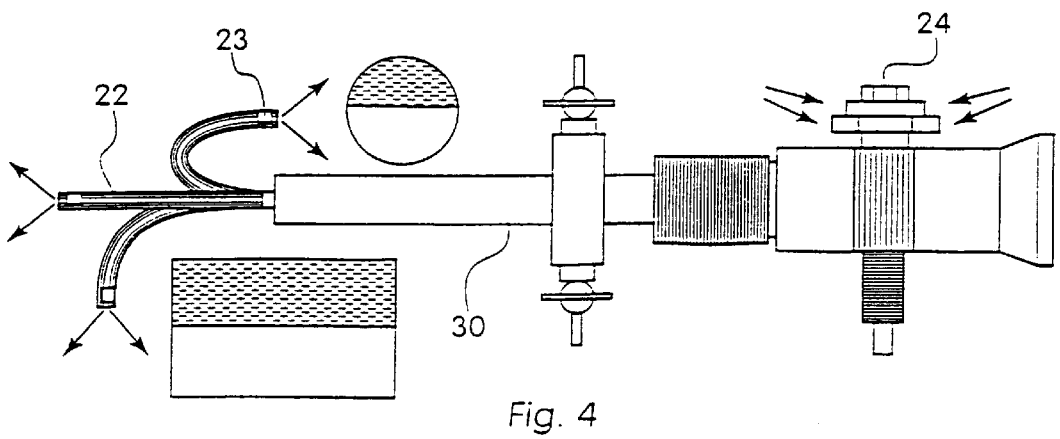
FIG. 4 is a partial side view of the endoscope and cannula according to FIG. 3b, showing different positions of the flexible fiber optic tip.

In the cannula-retracted position, flexible fiber optic tip 22 with lens 23 extends beyond cannula 30. FIG. 4 illustrates the positioning possibilities of flexible fiber optic tip 22 while it is extended beyond the distal tip of cannula 30. Turning knobs 24 causes tip 22 to move in a selected direction. The viewer turns knobs 24 until a desired position of tip 22 has been obtained. Knobs 24 also contain a locking mechanism that can lock tip 22 into a set position once that position has been obtained.

Figure 7:
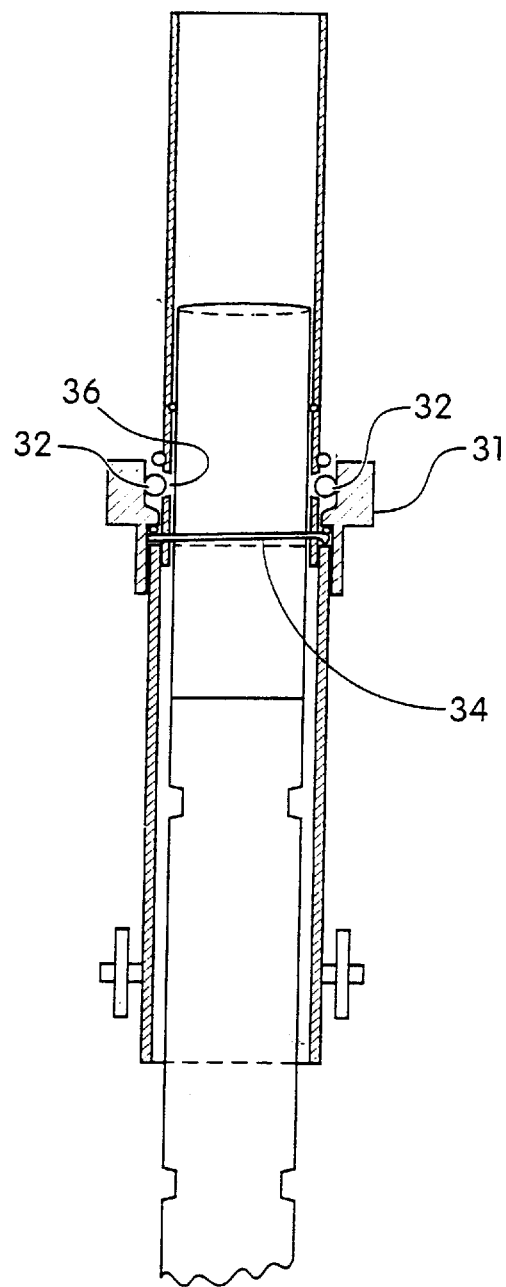
FIG. 7 is a longitudinal sectional view of the cannula and endoscope according to the present invention, showing the endoscope in an unlocked, movable position.

FIGS. 5–7 illustrate one embodiment of the dual positioning locking means on element 20 of endoscope 10 and element 25 of cannula 30, in a longitudinal sectional view. Element 25 has a circumferential snap coupling 31 arranged around its outer circumference and held in place by a pressurized spring 34. A plurality of ball bearings 32 are arranged in apertures 36 (shown in FIG. 7) around the circumference of element 25. In its resting position, snap coupling 31 contacts ball bearings 32 and presses them in toward the inner part of element 25. Ball bearings 32 are held in place by circumferential snap coupling 31.

Element 20 on endoscope 10 contains two grooves 26 arranged circumferentially around two different parts of element 20. During use, endoscope 10 is slid into cannula 30 until element 20 is inserted into element 25. Snap coupling 31 presses ball bearings 32 into the interior of element 25 so as to create a resistance against element 20 when it is inserted into element 25. When one of grooves 26 passes into the region of ball bearings 32, ball bearings 32 come to rest in groove 26 and lock the endoscope into place within the cannula.

If another position of endoscope 10 is desired, the ball bearings 32 may be released from groove 26 by pulling snap coupling 31 back against spring 34 to release the inward pressure on ball bearings 32. Element 20 on endoscope 10 can then be slid in either direction within element 25 until the desired groove is in the range of ball bearings 26. At this point, snap coupling 31 can be released to return to its resting position and to exert inward pressure on ball bearings 32 and lock endoscope 10 into place.

FIG. 5 shows this locking interaction with the endoscope 10 in a cannula retracted position, and FIG. 6 shows the locking interaction with endoscope 10 in the cannula-extended position. Movement between the cannula-retracted position and the cannula-extended position is illustrated in FIG. 7, in which snap coupling 31 is pulled back against spring 34 to release ball bearings 32 and to allow movement of the endoscope within the cannula.

As shown in FIGS. 5 and 6, a rubber O-ring 35 is placed around the inner circumference of the cannula and serves to seal the space between endoscope 20 and cannula 30 from moisture and/or water leakage.

Figure 8:
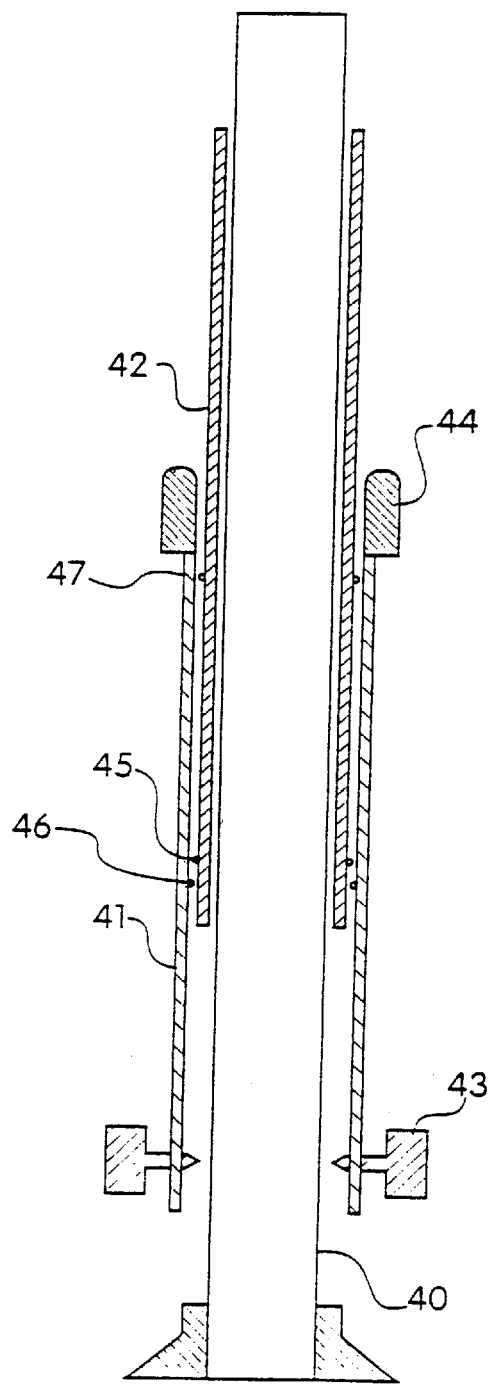
FIG. 8 is a longitudinal sectional view of an alternative embodiment of the cannula and endoscope of the present invention.
Figure 9:
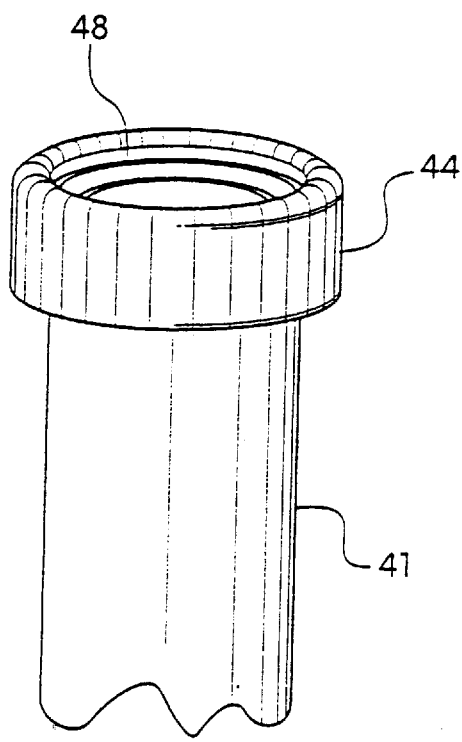
FIG. 9 is a side perspective view of the cannula locking mechanism of the embodiment shown in FIG. 8.

FIGS. 8 and 9 show an alternative embodiment of the cannula and endoscope of the present invention.

The cannula is comprised of telescoping parts 41 and 42, which are hollow tubes that slide relative to each other. Endoscope 40 is inserted into the cannula, and slides within parts 41 and 42. A locking device 43 locks endoscope 40 to part 41. Locking device 43 can be any known type of cannula locking device, such as that shown in U.S. Pat. No. 4,852,550.

A threaded compression nut 44 is mounted on the end of part 41, as shown in FIG. 9, and can selectively fix the positions of parts 41 and 42 with respect to each other. Turning nut 44 in one direction tightens nut 44 around part 42 and fixes the cannula position, and turning nut 44 in the other direction releases part 42 wherein it can slide within part 41 to another position. Elements 45, 46 and 47 are positioned in the space between parts 41 and 42 to limit the movement of parts 41 and 42. Elements 45, 46 and 47 can be any combination of protrusions, rubber O-rings, metal O-rings, or any type of moisture barrier-forming element, which prevents part 42 from sliding past a certain point on part 41, and keeps moisture and/or water from entering the space between the cannula and endoscope.

The tip of endoscope 40, as it is shown in FIG. 8, is extended beyond the end of the cannula. To move endoscope 40 into a retracted position so that its tip does not extend beyond the cannula, nut 44 is loosened and part 42 is slid within part 41 so that it covers the tip of endoscope 40.

Accordingly, while only several embodiments of the present invention have been shown and described, it is obvious that many changes and modifications may be made thereunto without departing from the spirit and scope of the invention.

What is claimed is:

1. An endoscopic device for viewing internal parts of a body, comprising:

an endoscope comprising:
(a) a rigid elongated tube having a proximal and a distal end;
(b) a control body attached to the proximal end of the elongated tube;
(c) an ocular eyepiece attached to the control body, said eyepiece adapted to permit viewing through the device to the distal end;
(d) a flexible fiber optic tip with a lens attached to the distal end of the rigid elongated tube;
(e) means for adjusting the position of the flexible fiber optic tip; and a cannula having a proximal end, a distal end, an outer circumference and an inner circumference, and adapted to receive the endoscope, comprising:
(a) a hollow tube;
(b) means for moving the endoscope within said cannula between a cannula-extended position and a cannula-retracted position; and (c) means for locking and unlocking the endoscope in the cannula-extended position and the cannula-retracted position, wherein in the cannula-extended position, the flexible tip is disposed entirely within the cannula and in the cannula-retracted position, the flexible tip extends beyond the distal end of the cannula.

2. The device of claim 1, wherein the means for adjusting the position of the flexible tip comprises a plurality of knobs located on the control body, wherein turning one or more knobs moves the flexible tip into different positions.

3. The device of claim 2, further comprising a locking device on the control body adapted to lock the flexible tip into a desired position.

4. The device of claim 1, wherein the means for locking the endoscope in a cannula-retracted and a cannula-extended position comprises:

at least one ball bearing mounted in at least one aperture arranged on the cannula;

a snap coupling arranged around the outer circumference of the cannula and adapted to exert inward pressure on the ball bearing;

a metal spring surrounding the outer circumference of the cannula and adapted to keep the snap coupling in contact with the ball bearing; and a ring arranged around the outer circumference of the cannula for retaining the ball bearing in its aperture in the cannula, said endoscope further comprising at least two circumferential grooves arranged around the endoscope, one groove adapted to lock the endoscope in a first position and the other groove adapted to lock the endoscope in a second position by engaging the ball bearing, said endoscope being moved between said first and second positions by retracting the snap coupling, the retraction of said snap coupling releasing the pressure on the ball bearing and allowing the endoscope to slide within the cannula until the ball bearing engages one of said at least two grooves.

5. The device according to claim 4, further comprising a rubber o-ring arranged around the inner circumference of the cannula, between the distal end of the cannula and the locking mechanism, said o-ring sealing the cannula against moisture and water.

6. A cannula for positioning a flexible-tipped endoscope comprising:

a hollow tube;

means for locking and unlocking the endoscope in two positions within the cannula, said first position being defined when the flexible tip of the endoscope is located entirely within the cannula, and said second position being defined when the flexible tip of the endoscope extends beyond the cannula.

7. The cannula of claim 6, wherein the means for locking the endoscope comprises an extension tube adapted to be inserted into the hollow tube and which is telescopically slidable within the hollow tube, and a locking device adapted for fixing the position of the hollow tube with respect to the extension tube.

8. The cannula of claim 7, wherein the locking device comprises a threaded compression nut arranged around the circumference of the hollow tube, so that turning the compression nut in one direction fixes the position of the extension tube with respect to the hollow tube, and turning the compression nut in the opposite direction releases the extension tube and allows it to move relative to the hollow tube.

9. The cannula of claim 7, further comprising means for limiting the telescopic movement of the hollow tubes with respect to each other.

* * * * *